United States Patent [19]
Hartley

[11] Patent Number: 5,957,857
[45] Date of Patent: Sep. 28, 1999

[54] APPARATUS AND METHOD FOR AUTOMATIC SENSING THRESHOLD DETERMINATION IN CARDIAC PACEMAKERS

[75] Inventor: Jesse W. Hartley, Lino Lakes, Minn.

[73] Assignee: Cardiac Pacemakers, Inc., St. Paul, Minn.

[21] Appl. No.: 09/073,945

[22] Filed: May 7, 1998

[51] Int. Cl.$^6$ ............ A61B 5/0402; A61B 5/0456; A61B 5/0452

[52] U.S. Cl. ............ 600/521; 600/509; 600/517; 607/9

[58] Field of Search ............ 607/9; 600/509, 600/517, 521

[56] References Cited

U.S. PATENT DOCUMENTS

| | | |
|---|---|---|
| 3,927,677 | 12/1975 | Gobeli et al. . |
| 4,181,135 | 1/1980 | Andresen et al. . |
| 4,708,144 | 11/1987 | Hamilton et al. . |
| 4,779,617 | 10/1988 | Whigham . |
| 4,903,699 | 2/1990 | Baker, Jr. et al. . |
| 5,117,824 | 6/1992 | Keimel et al. . |
| 5,177,824 | 1/1993 | Ou . |
| 5,873,898 | 2/1999 | Hemming et al. . |

OTHER PUBLICATIONS

John H. Wilson et al. "Clinical Evaluation of an Automatic Sensitivity Adjustment Feature in a Dual Chamber Pacemaker" *Pace*, vol. 13, Oct. 1990, pp. 1220–1223.

Pan et al A Real Time QRS Detection Algorithm, *IEEE Trans. Biomed Eng.* vol. BME–32, No. 3, Mar. 1995 pp. 230–236.

*Primary Examiner*—William E. Kamm
*Assistant Examiner*—Carl H. Layno
*Attorney, Agent, or Firm*—Nikolai, Mersereau & Dietz, P.A.

[57] ABSTRACT

An automatic sensing system for an implantable cardiac rhythm management device comprises a variable gain amplifier and associated filters where the gain of the amplifier is adjusted as a function of the peak amplitude of a cardiac depolarization signal (either a P-wave or an R-wave) and especially the relationship of the peak value to a maximum value dictated by the circuit's power supply rail. The trip point comparator has its trip point adjusted as a function of the difference between the detected peak value of the signal of interest and the peak value of noise not eliminated by the filtering employed.

16 Claims, 2 Drawing Sheets

APPARATUS AND METHOD FOR AUTOMATIC SENSING THRESHOLD DETERMINATION IN CARDIAC PACEMAKERS

BACKGROUND OF THE INVENTION

I. Field of the Invention

This invention relates generally to on-demand implantable cardiac rhythm management devices, such as implantable pacemakers and automatic implantable cardiac defibrillators, and more particularly to a novel design of sensing circuitry for detecting the occurrence of cardiac depolarization, either P-waves or R-waves, in the presence of muscle noise and other ECG artifacts.

II. Discussion of the Prior Art

In implantable cardiac pacemakers and/or cardioverters/defibrillators employing an R-wave detector, or both an R-wave detector and a P-wave detector, it is imperative that R-waves and/or P-waves be reliably detected even in the presence of noise which may be picked up on the cardiac leads and delivered to the implanted device. Noise sources typically include 50 or 60 Hz power line noise, muscle noise, motion artifacts, baseline wander and T-waves. A cardiac event is sensed when the amplified and filtered input signal, such as a P-wave or an R-wave, exceeds an established threshold value which is generally programmed into the device at the time of implantation.

In accordance with the prior art, the sensing threshold is static in time. It is adjusted by the physician to a level that is considered to be the best compromise for sensing the R-waves or P-waves seen at the time of adjustment and for noise avoidance. If the gain (sensitivity) of the sense amplifier is set too high, noise may be able to trigger the comparator and give a false indication of a cardiac event. Alternatively, if the gain or sensitivity is set too low, a legitimate cardiac event may not be detected by the comparator.

It is known in the art to provide upper and lower target levels where the lower level is approximately one-half of the amplitude of the upper level. The automatic sensing system attempts to maintain the peak of the R-wave between these two target levels and ideally bumping the upper level. In this regard, reference is made to a paper entitled "Clinical Evaluation of an Automatic Sensitivity Adjustment Feature in a Dual Chamber Pacemaker" by Wilson et al., *Pace*, vol. 13, pp. 1220–1223, October 1990. In this paper, the threshold is described as being increased after a predetermined number of beats are found to exceed the upper target, and decreased when a second predetermined number of beats exceeds the lower but not the upper target. This arrangement has a significant drawback in that it gives a very slow response to changes in R-wave amplitude.

The Gobeli et al. U.S. Pat. No. 3,927,677 describes a system where the comparator trip point is varied to sense at some level above the average value of the input signal. This offers the advantage of providing noise immunity, particularly to continuous noise such as 50–60 Hz pickup from household appliances and the like. The Keimel U.S. Pat. No. 5,117,824 describes the concept of using a proportion, e.g., 75%, of the peak R-wave amplitude as the initial value of the comparator trip point. The initial value is made to decay to some minimum value over a time period of three seconds or less.

It is also known in the art to provide automatic gain control (AGC) to adjust the gain of a variable gain sense amplifier to effectively vary the sensitivity of the sense amplifier so that the cardiac depolarization signal stays within the dynamic range of the sense amplifier. In this regard, reference is made to the Hamilton et al. U.S. Pat. No. 4,708,144 and the Baker, Jr. et al. U.S. Pat. No. 4,903,699 and the Keimel et al. U.S. Pat. No. 5,117,824.

SUMMARY OF THE INVENTION

The present invention provides an improved automatic sensing system for an implantable cardiac rhythm management device in which the sensing threshold (both input amplifier gain and comparator trip point) are automatically set to optimally sense the P-wave or R-wave while rejecting noise. The system comprises amplifying and filtering means that receives both ECG signals and noise signals. The amplifying means is preferably a variable gain amplifier having a first input terminal for receiving a gain adjust signal. The output from the variable gain amplifier is bandpass filtered which attenuates, but does not totally eliminates, myopotential noise, 60 Hz interference, T-wave interference and baseline drift. The output from the bandpass filter is then rectified or otherwise signal processed so as to convert the P-wave or R-wave of either polarity to a unipolar representation thereof. A further low-pass filter is then used to provide smoothing by concentrating the energy of the desired signals while suppressing high frequency noise.

The output from the smoothing filter is applied to a first input of a trip point comparator. If the signal amplitude exceeds the trip point of that comparator, it produces an output indicative of a detected R-wave or P-wave as the case may be. The trip point for the comparator is determined by peak detecting the output from the smoothing filter. In particular, it provides a signal indicative of the peak value of the depolarization signals as well as the peak value of the noise signals occurring between two successive R-waves or P-waves. Using this information, the trip point value is computed as the peak noise value plus a fraction of the difference between the signal peak value and the noise peak value. The computed trip point value is then applied to the trip point comparator, via a delay line, thereby providing additional rejection of T-waves and other low frequency noise.

The gain of the input amplifier is adjusted by way of an automatic gain control loop. After the detection of a R-wave (or P-wave in the case of an atrial sense amplifier), a refractory period is initiated and, at its conclusion, the peak value of the R-wave subjected to a smoothing algorithm. If the smoothed peak value is lower than a predetermined amplitude limit determined by the power supply rail potential, the gain is increased by a predetermined step amount. If the smoothed peak value is at or exceeds an upper limit, a gain reduction is determined by measuring the amount of time that the smoothed R-wave peak value remains at the upper limit. The signal for increasing or decreasing the gain of the variable gain amplifier is applied to the gain adjust terminal thereof. In this fashion, the gain for the sensing amplifier is maintained at as high a value as possible without exceeding the power supply rail voltage for more than a predetermined time.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
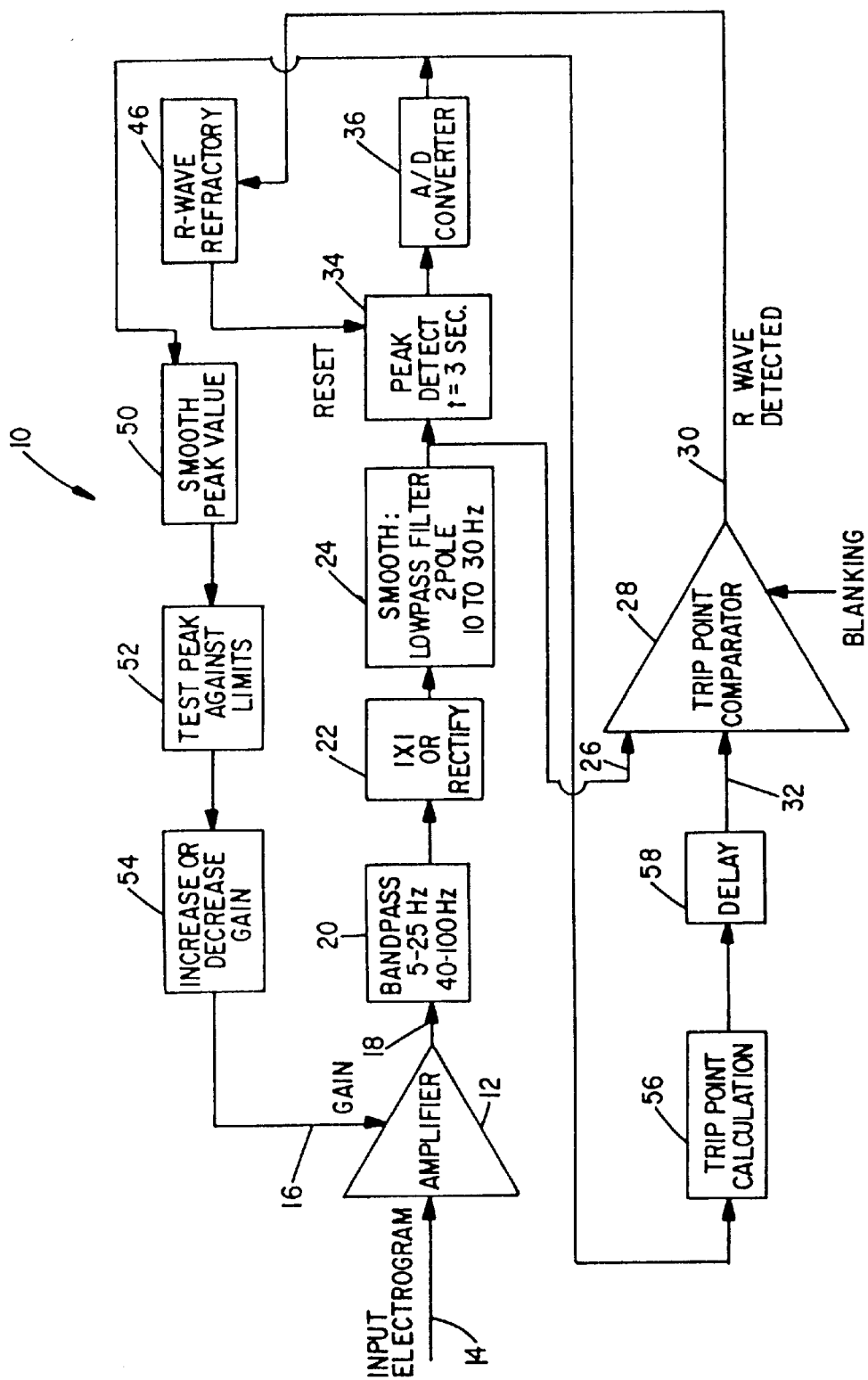
FIG. 1 is a block diagram of the automatic sensing system of the present invention.

Referring first to FIG. 1, there is indicated generally by numeral 10 an automatic sensing system for use in an implantable cardiac rhythm management device, such as a bradycardia pacer, an antitachy pacer or an implantable cardiac defibrillator. Comprising the system is an input amplifier 12 of the variable gain type having a first input 14 adapted to receive input electrogram signals picked up by electrodes positioned on or in a patient's heart. In the following explanation of the system, it will be assumed that it is an R-wave that is to be sensed in the presence of noise, but those skilled in the art will appreciate that the same system may be utilized in detecting P-waves in a dual chamber rhythm management device. The variable gain amplifier 12 has a gain adjust input 16 and an output terminal 18. Connected to the output terminal 18 of the amplifier 12 is a bandpass filter 20 whose upper and lower cut-off frequencies are specifically selected to attenuate T-waves on the low end and muscle noise and other environmental noise on the high end.

In that R-waves can be of either polarity, an absolute value circuit, such as a full wave rectifier 22, is connected to the output of bandpass filter circuit 20. The circuit 22 insures that the amplified and filtered input electrogram signal will be unipolar following rectification. A unipolar representation of the R-wave can also be achieved using a squaring function rather than rectification. In this regard, reference is made to a paper entitled "A Real-Time QRS Detection Algorithm", Pan and Thompkins, *IEEE Trans. Biomed. Eng.*, Vol. BME-32, No. Mar. 2, 1985. A squaring function is found to expand the dynamic range of the detection system while the absolute value or rectifier circuit 22 does not. In an implantable pacemaker, it is desirable to constrain the dynamic range to conserve power.

The output from the absolute value circuit 22 is then subjected to the action of a smoothing filter 24 which is preferably a two-pole, low-pass filter having a Butterworth filter characteristic to provide additional high frequency noise rejection. In this regard, the cut-off frequency is preferably somewhere in the range of from 10 Hz to 30 Hz. The Butterworth filter characteristic is chosen as a good compromise between phase linearity and transition band behavior.

The output from the smoothing filter 24 is connected to the signal input 26 of a trip point comparator 28. The trip point comparator 28 acts to produce an output on line 30 when the amplitude of the signal applied to input terminal 26 exceeds a variable threshold or trip point set by a signal coming in on the threshold input 32 thereof.

The output from the smoothing filter 24 is also applied to a peak detect circuit 34 which is used to find the peak value of the detected R-wave and also to measure the peak noise between two successive R-waves. The peak detector circuit 34 is preferably designed to have a decay time constant of about three seconds which is found to improve stability and recovery from noise impulses.

The peak value of the R-wave signal and noise is converted to a digital representation thereof in an A/D converter 36. While the A/D converter 36 is shown as being connected to the output of the peak detector 34, a workable system can be implemented by inserting the A/D converter 36 at the output of the bandpass filter 20 and, thus, the absolute value function, the smoothing and the peak detect function would all be done in the digital domain. In fact, the A/D conversion can take place following absolute value determination at block 22 or following the smoothing function at block 24.

Figure 2:
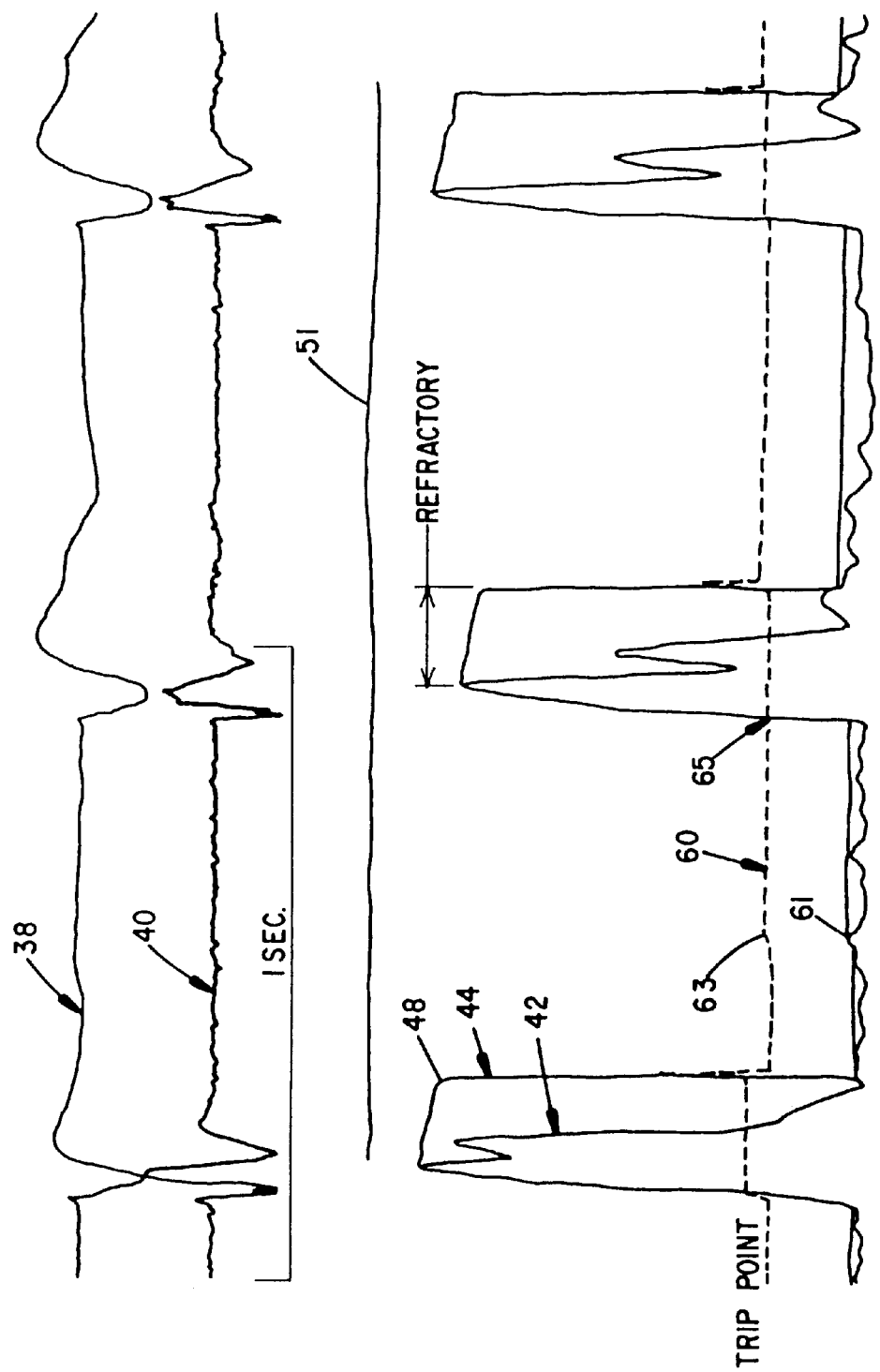
FIG. 2 shows a series of waveforms helpful in understanding the operation of the system of FIG. 1.

Referring momentarily to the waveforms of FIG. 2, the upper waveform 38 comprises the raw electrogram applied to the AGC amplifier 12 while waveform 40 represents the corresponding signal which will appear at the output of the bandpass filter 20 of FIG. 1. After the waveform 40 has passed through the absolute value circuit 22 and the smoothing filter 24, it has the wave shape identified by reference numeral 42. The output of the peak detector 34 is identified by reference numeral 44.

It should be mentioned at this point that the cardiac rhythm management device in which the automatic sensing system 10 of FIG. 1 is employed comprises microprocessor-based controller and, as such, includes a programmed microprocessor capable of executing a software program for appropriately adjusting the gain of the amplifier 12 and for determining the trip point for the trip point comparator 28. The upper feedback loop in FIG. 1 may, therefore, be implemented in software to perform the amplifier gain adjustment. After a sensed R-wave (or P-wave) is detected at the output 30 of the trip point comparator, a predetermined refractory period is initiated. The length of the refractory period may be about 100 milliseconds, which is purposely kept short to allow sensing during the main pacing refractory interval common to most dual chamber pacemakers and also to support sensing of high atrial or ventricular rates. The automatic sensing system of FIG. 1 is designed to exhibit settling times that are less than the 100 millisecond algorithmic refractory represented by block 46 in FIG. 1.

At the conclusion of the refractory interval, the digitized output of the peak detector is sampled at point 48 on waveform 44 and, as is indicated by block 50 in FIG. 1, is smoothed using a simple FIR digital filter, such as:

Smoothed Peak(t)=0.5*(Smoothed Peak(t-1)+Current R-Peak)

If the resulting smoothed peak value is determined to be lower than a predetermined lower amplitude limit, the gain of the amplifier 15 is increased by one incremental step. The need for a gain reduction is determined by measuring the amount of time that the smoothed R-wave peak is at an upper limit which, generally, is a function of the power supply rail voltage for the input amplifier 12 and is represented in FIG. 2 by horizontal line 51. In FIG. 1, the software step of testing the sampled peak R-wave value against upper and lower limits is represented by block 52 and the decision to increase or decrease the gain as a result of that test is indicated by block 54.

It can be seen, then, that the automatic sensing system 10 will tolerate some degree of clipping where the peak value of the R-wave hits the power supply rail. If clipping occurs, a counter may be started to determined the time that the peak value exceeds the power supply rail potential. If the time interval is greater than a predetermined limit, then the gain of the amplifier is decreased. Naturally, if the peak value is less than the limit, it is not necessary to decrease the gain. The object is to maintain the gain at as high a value as possible without exceeding the rail potential for more than a predetermined time interval.

The trip point for the comparator 28 is determined by the lower loop shown in FIG. 1. After the R-wave peak value has been sampled and processed by the upper gain adjust loop, the peak detector 34 is reset to continuously measure the peak noise between R-waves. The software step referred to as "Trip Point Calculation" (block 56) continuously operates to calculate from the value of the R-wave peak, and the currently measured peak noise by using the formula:

$$\text{Trip Point} = (R_p - N_p) * \text{Trip Fraction} + N_p$$

where Trip Fraction is a fraction of the distance between peak noise ($N_p$) and the peak value of the R-wave ($R_p$).

It can be seen from this equation that the calculated trip point is elevated above the observed noise level by the "Trip Fraction". The fraction used is a function of the observed noise level and varies from about 0.2 at low noise levels to about 0.4 at high noise levels. The trip fraction is thus made a function of noise level and changes with the amplitude of the noise. As the noise level increases, so does the trip fraction.

A delay in a range of from about 4 to 12 milliseconds is interposed (block 58) between the completion of the trip point calculation and the application of the resulting trip point value to the input 32 of the trip point comparator 28. This delay provides additional rejection of T-waves and low frequency noise. The delay 58 can follow a slowly increasing signal, allowing the trip point to ride on top of the noise as shown by the dashed line 60 in FIG. 2. Note especially that the noise peak level at 61 coincides with a shift in the trip point at 63. However, signals with high slew rates, such as R-waves, cannot be followed and if they are of sufficient amplitude, they will trigger the trip point comparator 28 as at 65 on trip point curve 60.

The algorithm is such that during the period following the termination of the refractory interval and the detection of a next R-wave event, if the noise level being measured becomes greater than one-half scale and if the R-wave peak amplitude is greater than, for example, 50 millivolts below the amplifier's rail potential, the operation indicated by block 54 causes the gain of the amplifier 12 to be reduced in order to correct for a possible error condition. Also, when the R—R escape interval expires and a pacing pulse is called for, it may be due to an inadequate gain in the amplifier 12 to sense the occurrence of a R-wave. Thus, on a pace condition, the gain is increased while the noise measuring function is continued. This performance, by itself, will cause the gain of the sense amplifier to go to a maximum in a patient experiencing no intrinsic cardiac activity or cardiac activity below a lower rate limit. The automatic sensing system 10 of the present invention deals with this tendency by checking for high noise level and large R-wave peaks, causing the gain of the amplifier 12 to be reduced. When a patient has some intrinsic activity, the upper gain adjust software loop will maintain itself. However, for patients with no intrinsic activity, it may be desirable to establish a maximum gain.

A continuous triggering of the comparator 28, meaning that the input remains above the trip point as in a high noise situation, causes the pacemaker to pace asynchronously. In these high noise situations, the auto sensing algorithm of the present invention will attempt to lower the gain of the amplifier 12 and raise the trip point of the comparator 28 in an effort to sense the R-wave in the presence of the high noise levels.

If the automatic sensing system of the present invention is to be implemented in a dual chamber pacemaker, conventional blanking techniques are utilized whereby pacing in an opposite chamber will create a blanking interval for the comparator 28. For example, if the automatic sensing system 10 is designed to detect atrial activity (P-wave), the sensing system for the atrial channel will be blanked upon the occurrence of a sensed event on the ventricular channel.

While there has been shown and described a preferred embodiment of the present invention, those skilled in the art can implement the invention in different ways. For example, the system may be implemented strictly using analog circuitry or, alternatively, may involve both analog circuitry and a digital implementation involving both digital hardware and software. Accordingly, the invention is to be limited only as dictated by the accompanying claims and the prior art.

What is claimed is:

1. An automatic sensing system for an implantable cardiac rhythm management device comprising in combination:
   (a) amplifying and filtering means for receiving ECG signals and noise signals, said amplifying and filtering means including
      (i) a variable gain amplifier having a first input terminal coupled to receive said ECG signals and said noise signals, a second input terminal for receiving a gain adjust signal and an output terminal;
      (ii) bandpass filter means coupled to said output terminal for attenuating said noise signals while passing said ECG signals;
      (iii) rectifier means coupled to said bandpass filter means for converting said ECG signals of either polarity to unipolar signals; and
      (iv) low pass filter means coupled to said rectifier means for attenuating said noise signals whose frequencies are above a predetermined cut-off frequency;
   (b) trip point comparator means having a signal input terminal, a trip point input terminal and an output terminal, said signal input terminal being coupled to an output of said low pass filter means, said trip point comparator producing an indication of a detected R or Q wave signal at said output terminal thereof when said output from said low pass filter means exceeds an adjustable trip point value applied to said trip point input terminal;
   (c) peak detector means coupled to receive the output of said low pass filter means for producing a voltage indicative of the peak value of said R or P wave signal and the peak value of noise signals occurring between successive R or P wave signals;
   (d) means coupled to said peak detector means for periodically computing said trip point value as a function of said peak value of said R or P wave signals and said noise signals occurring between successive R or P wave signals; and
   (e) means for applying said trip point value to said trip point input terminal.

2. The automatic sensing system as in claim 1 and further including an automatic gain control (AGC) loop and means for coupling said AGC loop between said peak detector means and said second input of said variable gain amplifier.

3. The automatic sensing system as in claim 2 wherein said AGC loop includes means for adjusting the level of a voltage applied to said second input of said variable gain amplifier, depending upon the relationship between said voltage produced by said peak detector means and a predetermined reference voltage.

4. The automatic sensing system as in claim 3 wherein said means for adjusting the level of the voltage applied to said second input of said variable gain amplifier determines the length of time that said voltage produced by said peak detector means equals or exceeds said reference voltage.

5. The automatic sensing system as in claim 1 and further including means for converting said voltage indicative of said peak value of said R or P wave signal to a digital representation thereof and said means for periodically computing said trip point value is a microprocessor.

6. The automatic sensing system as in claim 1 and further including means for converting said output of said low pass filter means to a digital representation thereof and said means for periodically computing said trip point value is a microprocessor.

7. The automatic sensing system as in claim 1 and further including means for converting an output signal from the rectifier means to a digital representation thereof and said means for periodically computing said trip point value is a microprocessor.

8. The automatic sensing system as in claim 1 and further including means for converting an output signal from the bandpass filter means to a digital representation thereof and said means for periodically computing said trip point value is a microprocessor.

9. The automatic sensing system as in claim 1 and further including delay means in said means for applying said trip point value to said trip point input terminal, said delay means effectively eliminating the effect of low slew rate signals, such as T-waves, on said adjustable trip point value.

10. The automatic sensing system as in claim 1 and further including refractory period establishing means coupled to said output terminal of said trip point comparator means for disabling said peak detector means for a predetermined interval starting with the detection of a R wave or a P wave signal on said output terminal of said trip point comparator.

11. The automatic sensing system as in claim 9 and further including an automatic gain control (AGC) loop and means for coupling said AGC loop between said peak detector means and said second input of said variable gain amplifier.

12. The automatic sensing system as in claim 11 wherein said AGC loop includes means for adjusting the level of a voltage applied to said second input of said variable gain amplifier depending upon the relationship between said voltage produced by said peak detector means and a predetermined reference voltage.

13. The automatic sensing system as in claim 12 wherein said means for adjusting the level of the voltage applied to said second input of said variable gain amplifier determines the length of time that said voltage produced by said peak detector means equals or exceeds said reference voltage.

14. An automatic sensing system for an implantable rhythm management device, comprising in combination:
   (a) variable gain amplifier means having an input terminal and an output terminal, said input terminal receiving ECG and noise signals from the body;
   (b) signal processing means coupled to said output terminal of said amplifier means for attenuating noise and T-wave components of said ECG signals and for converting R-waves in said ECG signals of either polarity to a unipolar representation thereof;
   (c) peak detecting means coupled to said signal processing means for measuring the peak value of said unipolar representations of said R-waves and peak values of said noise signals in the output from said signal processing means and producing voltage signals proportional to each;
   (d) comparator means coupled to the output from said signal processing means, said comparator means having an adjustable trip point; and
   (e) trip point determining means coupled to receive said voltage signals from the output of said peak detecting means for adjusting said trip point of said comparable means as a function of said peak value of said unipolar representations of R-waves and of noise signals said trip point determining means including delay means for enhancing rejection of said T-waves and noise signals whose frequencies are below the frequency of said R-waves.

15. The automatic sensing system as in claim 14 and further including an AGC loop coupled between said peak detecting means and said control input terminal of said variable gain amplifier means for adjusting the gain of said variable gain amplifier means based upon the length of time that the measured peak value of said unipolar representation of an R-wave exceeds a predetermined threshold value.

16. The automatic sensing system as in claim 14 wherein said trip point determining means includes means for calculating a trip point value in accordance with the formula:

$$\text{Trip Point} = (R_p - N_p) * \text{Trip Fraction} + N_p$$

where Trip Fraction is a fraction of the distance between the noise peak ($N_p$) and the peak value of the R-wave ($R_p$).

* * * * *